(12) United States Patent
Donald et al.

(10) Patent No.: US 9,681,903 B2
(45) Date of Patent: Jun. 20, 2017

(54) CLIP FOR DYNAMIC SPINAL PLATE

(71) Applicant: K2M, Inc., Leesburg, VA (US)

(72) Inventors: Gordon Donald, Red Bank, NJ (US); Jean Jacques Abitbol, Tampa, FL (US)

(73) Assignee: K2M, Inc., Leesburg, VA (US)

( * ) Notice: Subject to any disclaimer, the term of this patent is extended or adjusted under 35 U.S.C. 154(b) by 160 days.

(21) Appl. No.: 14/081,429

(22) Filed: Nov. 15, 2013

(65) Prior Publication Data

US 2015/0142062 A1    May 21, 2015

(51) Int. Cl.
   *A61B 17/80*      (2006.01)
   *A61B 17/70*      (2006.01)

(52) U.S. Cl.
   CPC ........ *A61B 17/808* (2013.01); *A61B 17/7059* (2013.01); *A61B 17/80* (2013.01)

(58) Field of Classification Search
   CPC ............. A61B 17/7059; A61B 17/80–17/8095
   See application file for complete search history.

(56) References Cited

U.S. PATENT DOCUMENTS

| | | | |
|---|---|---|---|
| 5,676,667 A * | 10/1997 | Hausman | 606/281 |
| 7,524,325 B2 | 4/2009 | Khalili | |
| 7,727,265 B2 | 6/2010 | Paul | |
| 8,636,738 B2 | 1/2014 | McClintock et al. | |
| 2004/0127899 A1 * | 7/2004 | Konieczynski | A61B 17/7059 606/281 |
| 2005/0283153 A1 * | 12/2005 | Poyner et al. | 606/61 |
| 2006/0217724 A1 | 9/2006 | Suh et al. | |
| 2006/0235398 A1 | 10/2006 | Farris et al. | |
| 2008/0108998 A1 | 5/2008 | Lindemann | |
| 2009/0076509 A1 | 3/2009 | Bush, Jr. et al. | |
| 2009/0281543 A1 * | 11/2009 | Orbay et al. | 606/70 |
| 2010/0204733 A1 * | 8/2010 | Rathbun et al. | 606/251 |
| 2012/0083846 A1 | 4/2012 | Wallenstein et al. | |
| 2013/0030465 A1 * | 1/2013 | Hess et al. | 606/246 |
| 2013/0110176 A1 * | 5/2013 | Rezach | A61B 17/7037 606/305 |

* cited by examiner

*Primary Examiner* — Nicholas Plionis
(74) *Attorney, Agent, or Firm* — Carter, DeLuca, Farrell & Schmidt, LLP (57) ABSTRACT

A clip includes a body and a pin. The body includes a first end, a second end, and a backspan extending between the first and second ends. The backspan defines a through hole. Each of the first and second ends of the body are configured to releasably couple to a rail of a dynamic spinal clip between two adjacent segments of a dynamic spinal clip to maintain a span between two adjacent segments. The pin defines a longitudinal axis and includes a head and a shaft. The shaft extends from the head to a tip. The tip is configured to penetrate bone. The shaft is configured and dimensioned to be slidably received through the through hole of the body The head is sized to prevent the head from passing through the through hole of the body.

13 Claims, 6 Drawing Sheets

CLIP FOR DYNAMIC SPINAL PLATE

BACKGROUND

1. Technical Field

The present disclosure relates to a device and instrument for use in orthopedic surgeries and, more specifically, to a clip that is selectively attachable to dynamic spinal plates and configured to maintain the dynamic spinal plates in an extended/expanded configuration.

2. Discussion of Related Art

The human spinal column is a highly complex structure. It includes twenty-four discrete bones, known as vertebrae, coupled sequentially to one another to house and protect critical elements of the nervous system. The cervical portion of the spine, which includes the neck of the spine up to the base of the skull, includes the first seven vertebrae.

For many reasons, such as aging and trauma, the intervertebral discs can begin to deteriorate and weaken. This may result in chronic pain, degenerative disc disease, or even tearing of the disc. Ultimately, the disc may deteriorate or weaken to the point of tearing and herniation, in which the inner portions of the disc protrude through the tear. A herniated disc may press against or pinch the spinal nerves, thereby causing radiating pain, numbness, and/or diminished strength or range of motion.

Many treatments are available to remedy these conditions, including surgical procedures in which one or more damaged intervertebral discs are removed and replaced with a prosthetic. However, should the prosthetic protrude from between the adjacent vertebrae and contact the surrounding nerves or tissues, the patient may experience additional discomfort. In procedures for remedying this problem, a spinal plate is affixed to the vertebrae and oriented to minimize such protrusion. In addition, the plate provides fixation and support to maintain spinal stability while the fusion occurs.

Spinal plates and cervical plates in particular, are known in the art. Fixed cervical plates generally exhibit unalterable, static dimensions. During the natural subsidence of the spinal column after surgery, the overall length of the spinal column gradually decreases. Fixed cervical plates resist this change due to their fixed axial length, which may eventually stress the spine and cause pain or discomfort. Adjustable or dynamic cervical plates attend to this predicament by providing a mechanism through which the plate is shortened to accommodate for a measure of subsidence.

During insertion it may be beneficial to prevent dynamic cervical plates from compressing.

SUMMARY

In an aspect of the present disclosure, a clip includes a body and a pin. The body includes a first end, a second end, and a backspan between the first and second ends. The backspan defines a through hole. Each end is configured to releasably couple to a rail of a dynamic spinal plate between adjacent segments of the dynamic spinal plate to maintain a span between the adjacent segments. The pin defines a longitudinal axis and includes a head and a shaft. The shaft extends from the head to a tip. The tip is configured to penetrate bone. The shaft is configured and dimensioned to be slidably received through the through hole of the body. The head is sized to inhibit the head from passing through the through hole of the body. The pin may include a biasing member disposed about the first portion that urges the head of the pin away from the backspan of the body.

In aspects of the present disclosure, the pin further includes a plate that is larger than the diameter of the through hole of the body and the backspan is disposed between the head and the plate with the first portion extending through the through hole. The second portion may include a groove and the plate may be seated within the groove.

In aspects of the present disclosure, the pin includes a third portion extending from the second portion along the longitudinal axis. The third portion includes a spiked end configured to engage a vertebra of a patient.

In aspects of the present disclosure, a kit includes a dynamic spinal plate and a clip. The dynamic spinal plate includes a first segment and a second segment moveable relative to one another between a distracted position and a compressed position. The first segment includes a pair of rails slidably received in the second segment. In the distracted position, a span is defined between the first segment and the second segment along a length of the pair of rails. The clip may be any of the clips described herein.

In aspects of the present disclosure, the dynamic spinal plate defines a space between two plate segments and the clip is positioned in the space. In embodiments, the space is defined within one of the first and second segments of the dynamic spinal plate. In some embodiments, the space is defined between one of the first and second segments and one of the pair of rails. The pair of rails may be adjacent an outer edge of the dynamic spinal plate.

In aspects of the present disclosure, the pin includes a spiked end. In a first position of the pin, the head is spaced apart from the backspan and the spiked end is between a bottom surface and a top surface of the dynamic spinal plate. In a second position of the pin, the head is in contact with the backspan and the spiked end extends beyond the bottom surface of the dynamic spinal plate.

In aspects of the present disclosure a method of spinal surgery includes inserting a dynamic spinal plate into a surgical site, maintaining a span between the first and second segments of the dynamic spinal plate with a clip between the first and second segments, securing the first segment to a first vertebra, securing the second segment to a second vertebra, and pulling a pin of the clip away from the surgical site to remove the clip from the dynamic spinal plate. The method may include impacting the head of the pin of the clip to partially secure the dynamic spinal plate to one of the first and second vertebrae before securing the first and second segments. The method may include aligning a drill guide with a screw hole of the dynamic spinal plate before securing the first and second segments. Aligning the drill guide may include engaging the pin of the clip with the drill guide. In embodiments, pulling the pin of the clip away from the surgical site includes engaging a backspan of the clip with a second portion of the pin.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 1:
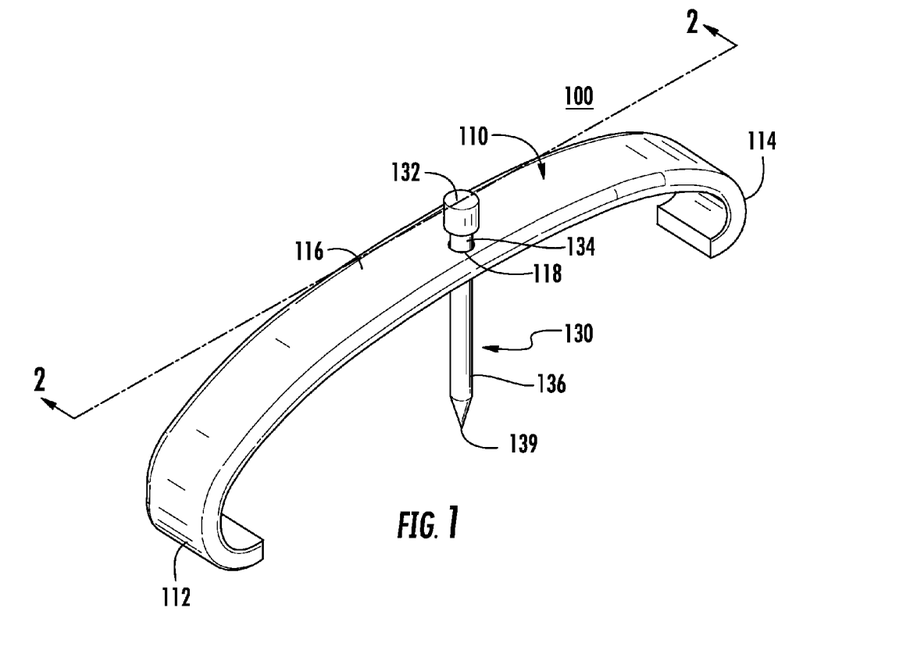
FIG. 1 is a perspective view of an exemplary embodiment of a clip provided in accordance with the present disclosure.
Figure 2:
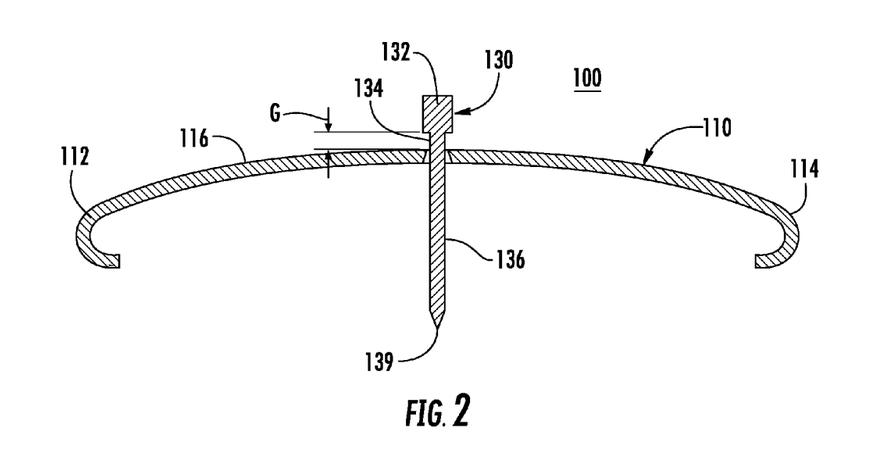
FIG. 2 is a side cross-sectional view taken along the line 2-2 shown in FIG. 1.

With reference to FIGS. 1 and 2, an exemplary embodiment of a clip 100 is provided in accordance with the present disclosure and includes a body 110 and a pin 130. The body 110 includes a first end 112, a second end 114, and a backspan 116 between the first and second ends 112, 114. Each end 112, 114 is configured to engage rails 21 (FIG. 3) of a dynamic spinal plate 10 (FIG. 3) as detailed below. The backspan 116 defines a through hole 118 that is substantially centered in and orthogonal to the backspan 116. The through hole 118 may be frustoconically shaped as best shown in FIG. 2. In embodiments, the through hole 118 has a substantially circular opening on the top surface of the backspan 116 and an oval opening in the lower surface of the backspan 116. In some embodiments, the through hole 118 is cylindrical. In certain embodiments, through hole 118 defines an angle relative to the top and bottom surfaces of the dynamic spinal plate 10.

The pin 130 includes a head 132, a first portion 134, a second portion 136, and a spiked end 139. The head 132 is larger than the through hole 118 such that the head 132 is inhibited from passing through the through hole 118. The first portion 134 extends downward (as shown in FIG. 2) from the head 132 and is slidably received within the through hole 118. The second portion 136 extends downward (as shown in FIG. 2) from the first portion 134. The second portion 136 may be larger than the through hole 118 such that the second portion 136 is inhibited from passing through the through hole 118. The spiked end 139 extends downward (as shown in FIG. 2) from the second portion 136. The head 132 and the first portion 134 may be integrally formed with one another. The pin 130 may be assembled as a two piece assembly. In embodiments, the head 132 and the first portion 134 are joined together by at least one of a friction fit, cooperating threads, welding, an eye and retaining pin, or any other known means of joining the head 132 to the first portion 134. The first and second portions 134, 136 may be integrally formed with one another. In some embodiments, the first portion 134 and the second portion 136 are joined together by at least one of a friction fit, cooperating threads, welding, an eye and retaining pin, or any other suitable means.

With particular reference to FIG. 2, the pin 130 is slidably received through the through hole 118 in the backspan 116. When the first portion 134 of the pin 130 is received within the through hole 118 of the backspan 116 of the body 110, the head 132 of the pin 130 defines a gap G with the backspan 116 of the body 110. The pin 130 is slidable between a first position and a second position. In the first position, the gap G has maximum dimension. In the second position, the head 132 is in contact with the backspan 116 such that the gap G has a minimum dimension. As shown, the minimum dimension of the gap G is about 0 mm and the maximum dimension of the first gap $G_1$ is about 15 mm; however, the maximum dimension of the gap G may be in a range of about 1 mm to about 15 mm. When the pin 130 is inserted through the through hole 118, the pin 130 may engage a vertebra 1000 cephalad or caudad the position of the through hole 118 to partially secure the dynamic spinal plate 10 to the vertebra 1000 as detailed below.

Figure 3:
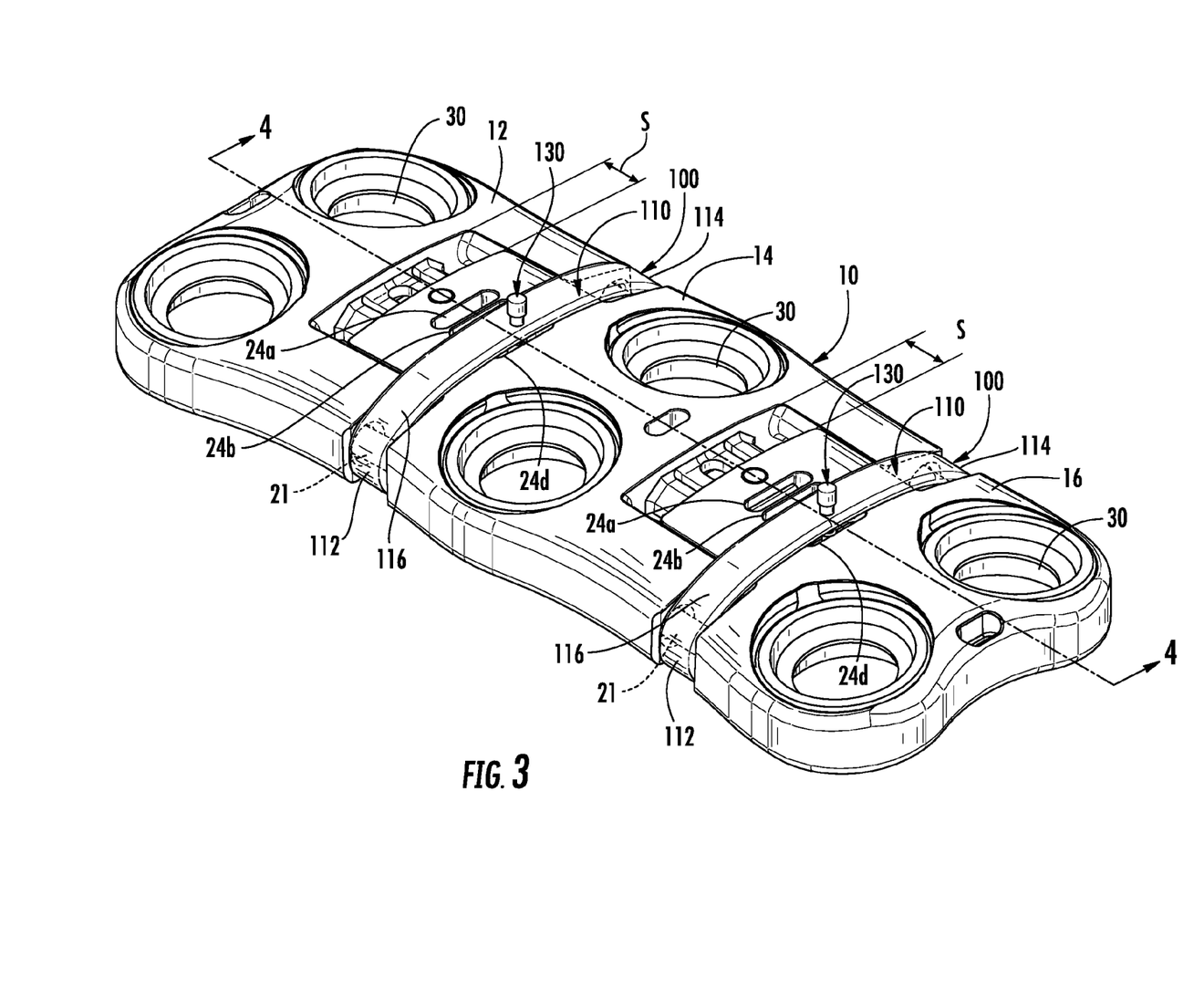
FIG. 3 is a perspective view of the clip of FIG. 1 coupled to rails of a dynamic spinal plate.

Referring to FIG. 3, the clip 100 is engaged with rails 21 of a dynamic spinal plate 10. The plate 10 includes a first segment 12, a central segment 14, and a second segment 16. The segments 12, 14, 16 are longitudinally moveable relative to one another between a distracted position and a collapsed position. In the distracted position, the segments 12, 14, 16 are spaced apart from one another defining a span S between adjacent segments 12, 14, 16. In the collapsed position, the segments 12, 14, 16 the span S between adjacent segments 12, 14, 16 are substantially or completely closed. It is contemplated that two adjacent segments, e.g., segments 12 and 14, may be in a distracted position and two other adjacent segments, e.g., segments 14 and 16, may be in a collapsed position. The segments 12, 14, 16 of the plate 10 are configured to allow adjacent segments to move towards the collapsed position and inhibit adjacent segments from moving towards the distracted position during installation and in response to subsidence of a patient's spine. Such a spinal plate is disclosed in co-owned U.S. patent application Ser. No. 12/766,438 filed Apr. 23, 2010, and Ser. No. 13/251,622 filed Oct. 3, 2011, the content of each is incorporated in its entirety.

The first and second ends 112, 114 of the clip 100 are sized and configured to selectively engage rails 21 (shown in phantom) between adjacent segments 12, 14, 16 of the plate 10 to prevent the adjacent segments 12, 14, 16 from moving towards the collapsed position, i.e., clip 100 maintains a span between adjacent segments 12, 14, 16. It is contemplated that the body 110 may be sized to prevent adjacent segments 12, 14, 16 from additional movement towards the collapsed position after initial movement from the distracted position towards the collapsed position.

Figure 4:
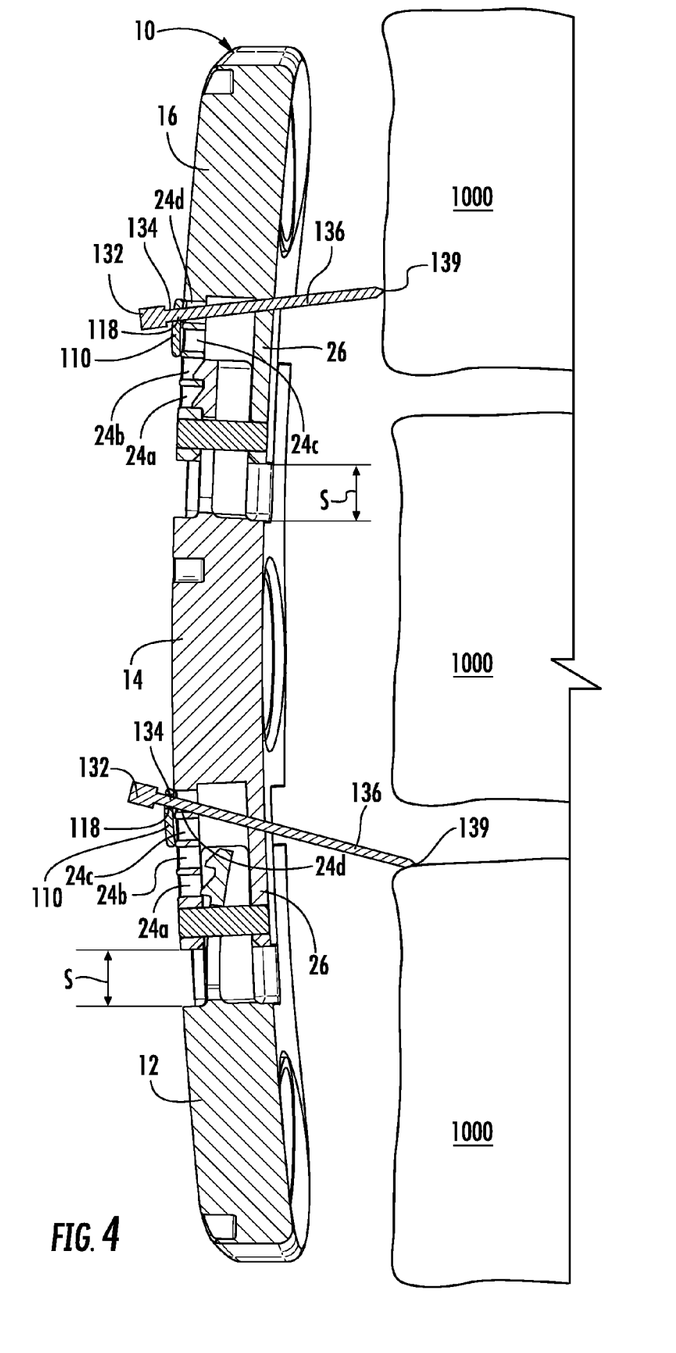
FIG. 4 is a side cross-sectional view of the dynamic spinal plate taken along the line 4-4 shown in FIG. 3 with the pins of the clip engaged with vertebrae of a patient.

With reference to FIG. 4, at least one of the portions 134, 136 of the pin 130 passes through one of slots 24a-d in the top surface of the plate 10. At least one of the portions 134, 136 of the pin 130 may pass through an opening 26 in the bottom surface of the plate 10. When the clip 100 is engaged with plate 10 and the pin 130 is in the second position, the spiked end 139 of the pin 130 extends below the bottom surface of the plate 10 and may engage vertebrae 1000 as detailed below. When the clip 100 is engaged with the plate 10 and the pin 130 is in the first position, the end of spiked end 139 is at or above the bottom surface of the plate 10.

In use, the clip 100 is installed into the span S between two adjacent segments 12, 14, 16 of the spinal plate by engaging rails 21 with ends 112, 114 of the clip 100 before the plate 10 is inserted into a surgical site. The clip 100 may be installed at the time of manufacturing and provided as part of a kit with the plate 10. The clip 100 may be installed by a clinician prior to the insertion of the plate 10 into a surgical site. The pin 130 may be preloaded in the clip 100. When the clip 100 is installed into the span S between two adjacent segments 12, 14, 16, the plate 10 is inserted into a surgical site and aligned with vertebrae 1000 to be engaged with the plate 10. As the plate 10 is aligned with the vertebrae 1000, the spiked end 139 of the pin 130 may contact the vertebrae urging the pin 130 towards the first position. When the plate 10 is aligned with the vertebrae, the surgeon may impact or tap the head 132 of the pin 130 with an instrument, e.g., a hammer (not shown), to drive the spiked end 139 into the vertebra 1000 to partially secure the plate 10 to the vertebrae as shown in FIG. 4, similar to a center punch. The surgeon may impact the head 132 of pin 130 of multiple clips 100 to partially secure the plate 10 to the vertebrae 1000; in such embodiments, the pins 130 of the multiple clips 100 may engage the same or different vertebra 1000. The surgeon may install a drill guide (not shown) on or about plate 10. When the drill guide is installed on or about plate 10, the drill guide is aligned with a screw hole 30 defined by the plate 10. The drill guide may engage the head 132 or a portion 134, 136 of the pin 130 of a clip 100 to align the drill guide with the screw hole 30. When the drill guide is aligned with the screw hole 30, the surgeon utilizes the drill guide to drill a drill hole (not shown) in a vertebra through the screw hole 30. The surgeon repeats the aligning the drill guide and drilling for each screw hole 30 of the plate 10. In embodiments, the drill guide is rotated about the pin 130 to align the drill guide with another screw hole 30 after a drill hole is drilled. A bone screw (not shown) is then inserted into each drill hole through a respective screw hole 30 of the plate 10 to secure the plate 10 to the vertebrae. After the plate 10 is secured to the vertebrae 1000, the head 132 of the pin 130 is engaged with a tool, e.g., needle remover, coker clamp, etc., to pull the head 132 away from the plate 10. As the head 132 is pulled, a portion 134, 136 may engage the backspan 116 of the body 110 of the clip 100 to disengage the first and second ends 112, 114 from rails 21 of the plate 10 to remove the clip 100 from the plate 10. After the clip 100 is removed, the adjacent segments 12, 14, 16 are free to move towards the compressed position.

Figure 5:
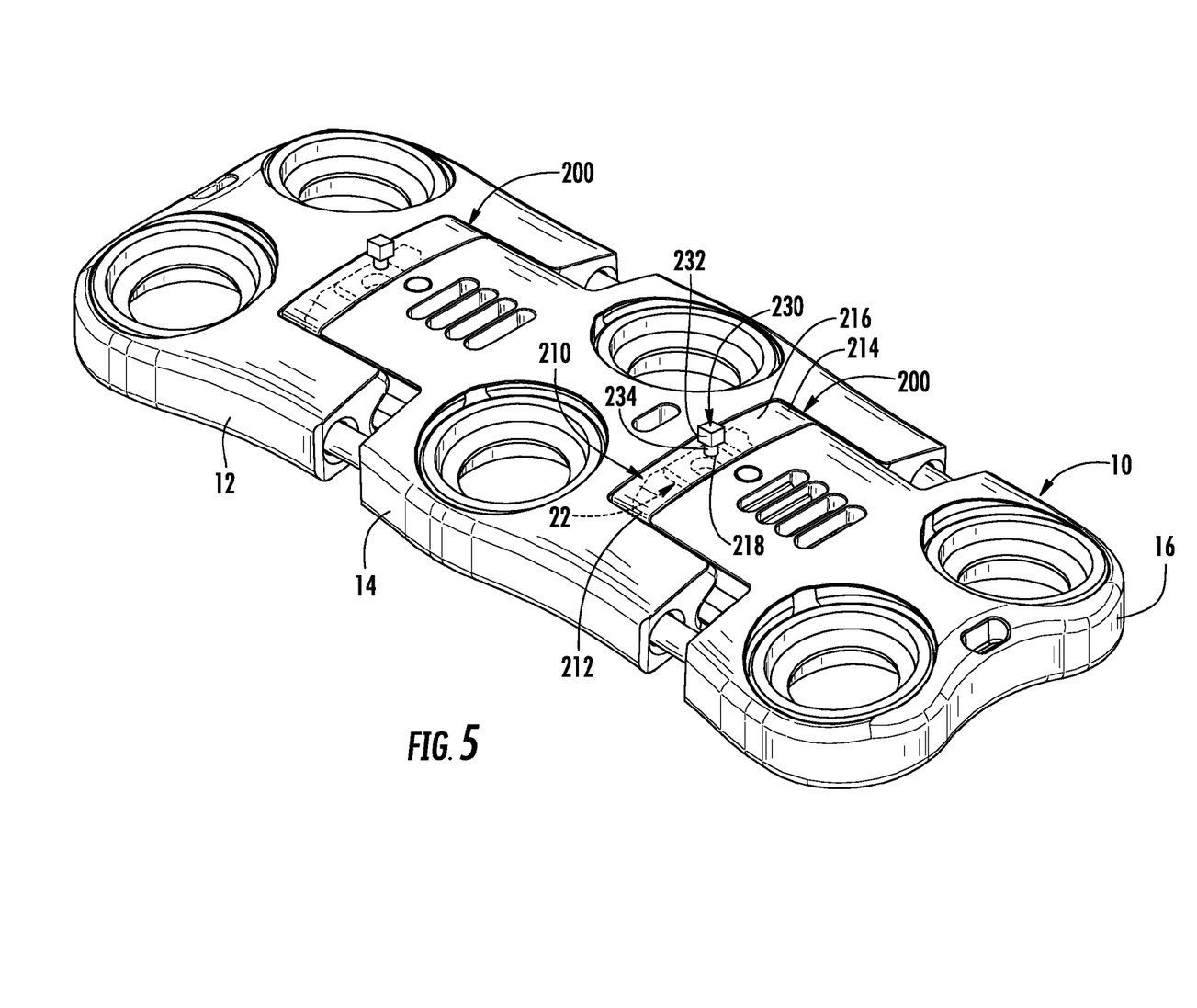
FIG. 5 is a perspective view of another exemplary embodiment of a clip provided in accordance with the present disclosure coupled to a dynamic spinal plate.

Referring to FIG. 5, an exemplary embodiment of a clip 200 is provided in accordance with the present disclosure is installed in a span S on rails 22 between two adjacent segments 12, 14, 16 of a plate 10. The clip 200 includes a body 210 and a pin 230. The body 210 and the pin 230 of the clip 200 are substantially similar to the body 110 and the pin 130 of the clip 100 described above, as such only the differences will be detailed below.

First and second end portions 212, 214 of the body 210 include flat angular surfaces to conform to the outside surface of rails 22 (shown in phantom). A backspan 216 of the body 210 conforms to the span between rails 22. A through hole 218 in the backspan 216 is cylindrically shaped. The first portion 234 of the pin 230 is cylindrically shaped and sized to be slidably received within the through hole 218. A head 232 of the pin 230 is square shaped and sized to prevent the head 232 from passing through the through hole 218, i.e., retain the first portion 234 within the through hole 218.

Figure 6:
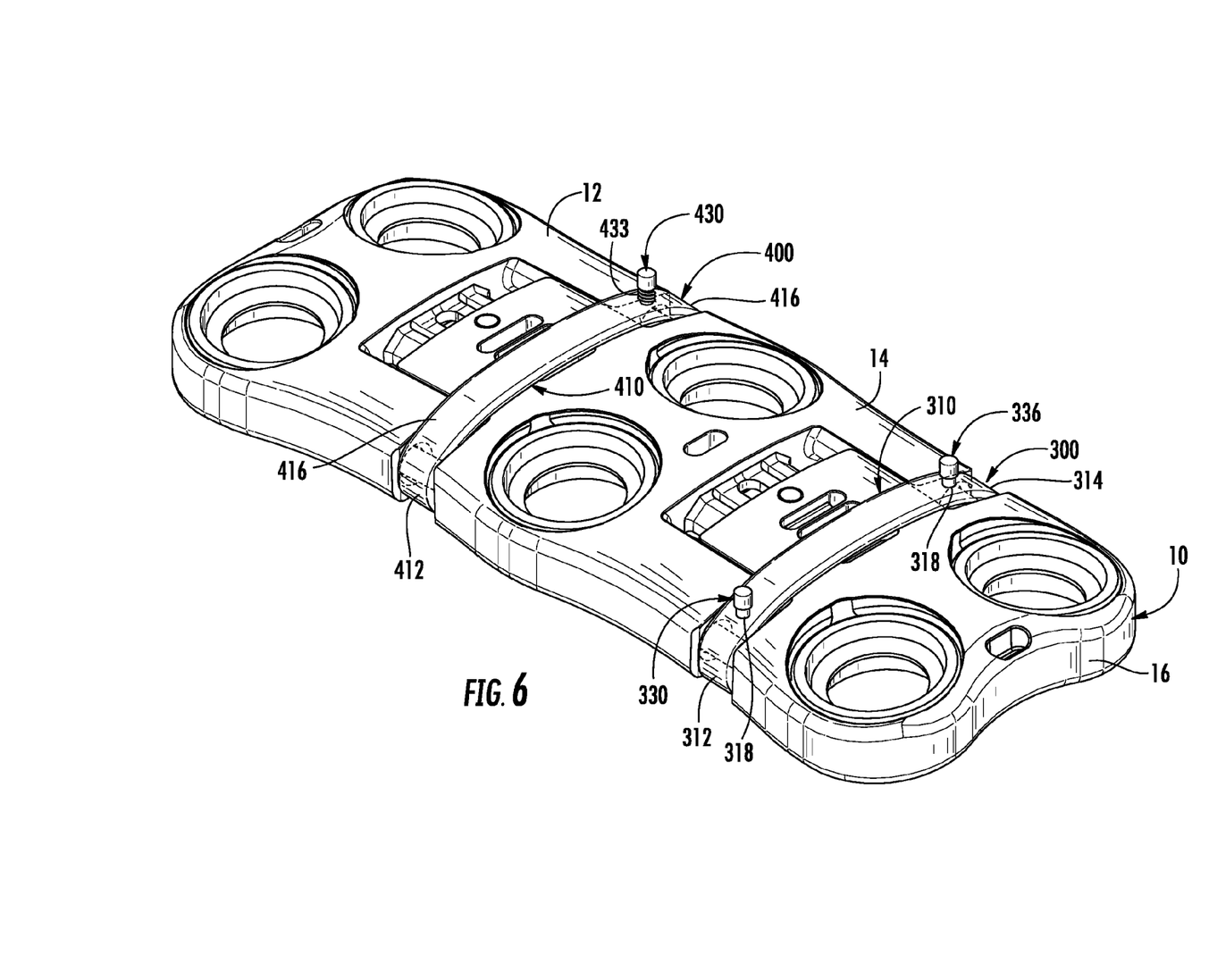
FIG. 6 is a perspective view of additional exemplary embodiments of a clips provided in accordance with the present disclosure coupled to a dynamic spinal plate.

Referring to FIG. 6, exemplary embodiments of a clip 300 and a clip 400 are provided in accordance with the present disclosure and are installed in respective spans between two adjacent segments 12, 14, 16 of a plate 10. The clip 300 includes a body 310 and two pins 330. The clip 400 includes a body 410 and a pin 430. The body 310 and each pin 330 of the clip 300 and the body 410 and the pin 430 of clip 400 are substantially similar to the body 110 and the pin 130 of the clip 100 described above, respectively, as such only the differences will be detailed below.

The body 310 of the clip 300 includes a backspan 316 defining two through holes 318 near end portions 312 and 314 respectively. A pin 330 is received through each of the through holes 318 such that when a head 332 of one of the pins 330 is pulled away from the plate 10 the respective end 312, 314 disengages the respective rail 21. The pin 330 passes through a spaced defined between the respective rail 21 and the segment 16 of the plate 10. It is contemplated that when the head 332 of one of the pins 330 is pulled away from the plate 10 each end 312, 314 may disengage the respective rail 21. Providing multiple pins in a clip may assist a surgeon in partially securing the plate 10 to the vertebrae before securing the plate to the vertebrae with the bone screws (not shown) as described above by providing multiple spiked ends to engage the vertebrae. In addition, providing multiple pins in a clip may assist in aligning a drill guide (not shown) with the screw holes of the plate.

The body 410 of the clip 400 includes a backspan 416 defining a through hole 418 adjacent one of end portions 412, 414. The pin 430 passes through the through hole 418 and through a spaced defined between the respective rail 21 and segment 14 of plate 10. The clip 400 may include a pin biasing member 433 disposed about the pin 430 between a head 432 of the pin 430 and the backspan 416 of the clip 400. The pin biasing member 433 urges the pin 430 towards the first position as detailed above with respect to the pin 130. When the head 432 of the pin 430 is pulled away from the plate 10, the second end 414 disengages a respective rail 21 and then the clip 400 is manipulated to disengage the first end 412 from its respective rail 21.

Figure 7:
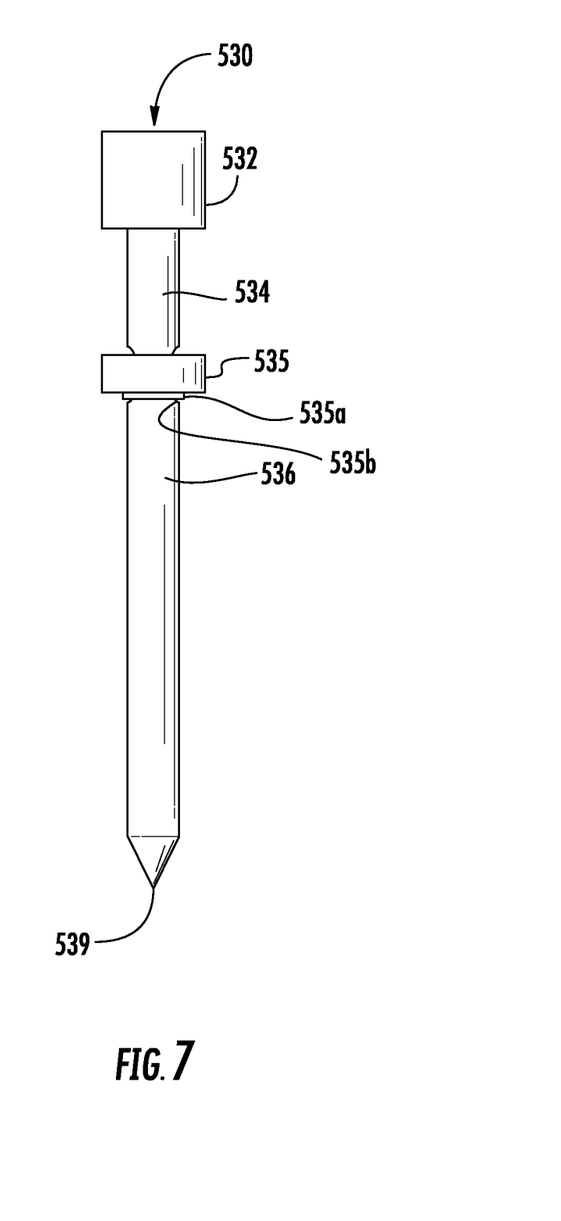
FIG. 7 is a side view of another embodiment of a pin in accordance with the present disclosure for use with a clip.

Referring to FIG. 7, another embodiment of a pin 530 in accordance with the present disclosure may be used with any of the clips 100, 200, 300, and 400 detailed above. The pin 530 includes a pin head 532, a first portion 534, a plate or disc 535, a second portion 536, and a spiked end 539. The pin head 532 is sized and/or shaped to prevent the pin head 532 from passing through a through hole in the backspan of the body of a clip, e.g., through hole 118 (FIG. 1). The first portion 534 is sized and shaped to be slidably received through the through hole in the backspan. The plate 535 is slidably received over the first portion 534 adjacent the second portion 536. The pin 530 may include a stop 535a positioned adjacent the second portion 536. The stop 535a prevents the plate 535 from sliding over the second portion 536. The stop 535a may seat in a groove 535b adjacent the junction of the first and second portions 534, 536. The stop 535a may be a snap ring seated in the groove. In some embodiments, the plate 535 is positioned at the junction of the first and second portions 534, 536 and is sized and configured to prevent the second portion 536 from passing through the through hole in the backspan of the body. In particular embodiments, the plate 535 seats in a groove 535b at the junction of the first and second portions 534, 536. The spiked end 539 is substantially similar to the spiked end 139 of the pin 130 detailed above.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A clip comprising:
   a body including a first end, a second end, and a backspan between the first and second ends, the backspan defining a through hole, each end configured to releasably couple to a rail of a dynamic spinal plate between adjacent segments of the dynamic spinal plate to maintain a span between the adjacent segments;
   a pin defining a longitudinal axis and including a head and a shaft extending from the head to a tip, the tip configured to penetrate bone and the shaft configured and dimensioned to be slidably received through the through hole of the body, the head sized to inhibit the head from passing through the through hole of the body; and
   a disc disposed about the shaft, the disc having a constant inner dimension larger than a diameter of the through hole to retain the pin within the through hole of the body, the entire backspan of the body positioned between the disc and the head.

2. The clip of claim 1, wherein the tip of the pin is configured to engage a vertebra of a patient.

3. The clip of claim 1, wherein the pin includes a biasing member disposed about the first portion to urge the head of the pin away from the backspan.

4. The clip of claim 1, wherein the through hole is frustoconically shaped.

5. The clip of claim 1, wherein the shaft includes a first portion adjacent the head and a second portion extending from the first portion to the tip.

6. The clip of claim 5, wherein the disc is slidable over the first portion.

7. The clip of claim 5, wherein the second portion defines a groove, the disc seated within the groove.

8. A kit comprising:
   a dynamic spinal plate including a first segment and a second segment moveable relative to one another between a distracted position and a compressed position, the first segment including a pair of rails slidably received in the second segment, wherein in the distracted position a span is defined between the first segment and the second segment along a length of the pair of rails; and
   a clip including:
     a body including a first end, a second end, and a backspan between the first and second ends, the backspan defining a through hole, the first and second ends releasably coupled to the pair of rails of the dynamic spinal plate in the span between the first and second segments of the dynamic spinal plate to prevent the dynamic spinal plate from moving towards the compressed position;
     a pin defining a longitudinal axis and including a head and a shaft extending from the head to a tip configured to penetrate bone, the shaft slidably received through the through hole of the body, the head sized to prevent the head from passing through the through hole of the body; and
     a rigid disc disposed about the shaft of the pin and configured to retain the entire backspan of the body between the head and the disc.

9. The kit of claim 8, wherein the dynamic spinal plate defines a space between two plate segments, the clip positioned in the space.

10. The kit of claim 9, wherein the space is defined within at least one of the first and second segments.

11. The kit of claim 9, wherein the space is defined between at least one of the first and second segments and one of the pair of rails.

12. The kit of claim 8, wherein has a first position, wherein the head is spaced apart from the backspan and the tip is between a bottom surface and a top surface of the dynamic spinal plate, and a second position, wherein the head is in contact with the backspan and the tip extends beyond the bottom surface of the dynamic spinal plate.

13. The kit of claim 8, wherein each of the pair of rails is adjacent an outer edge of the dynamic spinal plate.

* * * * *